US010842801B2

(12) United States Patent
Belanoff et al.

(10) Patent No.: US 10,842,801 B2
(45) Date of Patent: *Nov. 24, 2020

(54) OPTIMIZING MIFEPRISTONE ABSORPTION

(71) Applicant: Corcept Therapeutics, Inc., Menlo Park, CA (US)

(72) Inventors: Joe Belanoff, Menlo Park, CA (US); Robert Roe, Menlo Park, CA (US); Caroline Loewy, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/574,780

(22) Filed: Sep. 18, 2019

(65) Prior Publication Data

US 2020/0009159 A1 Jan. 9, 2020

Related U.S. Application Data

(63) Continuation of application No. 13/677,465, filed on Nov. 15, 2012, now Pat. No. 10,500,216.

(60) Provisional application No. 61/561,644, filed on Nov. 18, 2011.

(51) Int. Cl.
*A61K 31/575* (2006.01)
*A61K 31/567* (2006.01)

(52) U.S. Cl.
CPC .......... *A61K 31/575* (2013.01); *A61K 31/567* (2013.01)

(58) Field of Classification Search
CPC .......................... A61K 31/567; A61K 31/575
See application file for complete search history.

(56) References Cited

U.S. PATENT DOCUMENTS

| | | | |
|---|---|---|---|
| 6,150,349 | A | 11/2000 | Schatzberg et al. |
| 6,369,046 | B1 | 4/2002 | Schatzberg et al. |
| 6,620,802 | B1 | 9/2003 | Schatzberg et al. |
| 6,680,310 | B2 | 1/2004 | Belanoff et al. |
| 6,964,953 | B2 | 11/2005 | Belanoff |
| 7,163,934 | B2 | 1/2007 | Belanoff |
| 7,326,697 | B2 | 2/2008 | Schatzberg et al. |
| 7,361,646 | B2 | 4/2008 | Belanoff |
| 7,402,578 | B2 | 7/2008 | Belanoff |
| 8,097,606 | B2 | 1/2012 | Belanoff |
| 8,598,149 | B2 | 12/2013 | Belanoff |
| 8,921,348 | B2 | 12/2014 | Belanoff |
| 9,943,526 | B2 | 4/2018 | Belanoff et al. |
| 10,166,242 | B2 | 1/2019 | Belanoff et al. |
| 10,166,243 | B1 | 1/2019 | Belanoff et al. |
| 2004/0132703 | A1 | 7/2004 | Belanoff |
| 2004/0229855 | A1 | 11/2004 | Belanoff |
| 2006/0063748 | A1 | 3/2006 | Belanoff |
| 2007/0238779 | A1 | 10/2007 | Roberts et al. |
| 2007/0254025 | A1 | 11/2007 | Cronk |
| 2010/0179115 | A1 | 7/2010 | Belanoff |
| 2010/0261693 | A1 | 10/2010 | Ulmann et al. |
| 2011/0144072 | A1 | 6/2011 | Belanoff |
| 2011/0166115 | A1 | 7/2011 | Belanoff |
| 2011/0294771 | A1 | 12/2011 | Belanoff |
| 2013/0131030 | A1 | 5/2013 | Belanoff et al. |
| 2014/0162993 | A1 | 6/2014 | Belanoff |
| 2016/0310507 | A1 | 10/2016 | Belanoff et al. |

FOREIGN PATENT DOCUMENTS

| | | |
|---|---|---|
| WO | 01/80896 A2 | 11/2001 |
| WO | 2009050136 A2 | 4/2009 |
| WO | 2010/138758 A1 | 12/2010 |

OTHER PUBLICATIONS

"Food-Effect Bioavailability and Fed Bioequivalence Studies", Guidance for Industry: U.S. Department of Health and Human Services, Food and Drug Administration, Center for Drug Evaluation and Research (CDER), Dec. 2002, 12 pages.

Medical Encyclopedia: Therapeutic Drug Levels, MedlinePlus, Available online at: http://www.nlm.nih.gov/medlineplus/ency/article/003430.htm, Oct. 2005, 4 pages.

The Biopharmaceutics Classification System (BCS) Guidance, Available on Internet at: https://www.fda.gov/AboutFDA/CentersOffices/OfficeofMedicaiProductsandTobacco/CDER/ucm128219.htm, Accessed from internet on Oct. 17, 2017, 4 pages.

The New Drug Application (NDA) BA and BE Draft Guidance (Guidance for Industry. Bioavailability and Bioequivalence Studies Submitted in NDAs or INDs—General Considerations, U.S. Department of Health and Human Services, Food and Drug Administration, Center for Drug Evaluation and Research, Biopharmaceutics, https://www.fda.gov/downloads/drugs/guidancecomplianceregulatotyinformation/guidances/ucm389370.pdf, Mar. 2014, 29 pages.

Chu et al., "Successful Long-Term Treatment of Refractory Cushing's Disease with High-Dose Mifepristone (RU 486)", The Journal of Clinical Endocrinology & Metabolism, vol. 86, Issue No. 8, Aug. 2001, pp. 3568-3573.

Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6 http://dx.doi.org/10.1210/jc.2011-3550, Jun. 2012, pp. 2039-2049.

Gross et al., "Mifepristone Reduces Weight Gain and Improves Metabolic Abnormalities Associated With Risperidone Treatment in Normal Men", Obesity, vol. 18, Issue No. 12, Dec. 2010.

Hofsaess et al., "Establishing the BCS Classification of APis Recently Added to the WHO Essential Medicines List", Poster Presentation at the 2015 AAPS Annual Meeting and Exposition, St. Louis, MO, Poster T2064, 2015, 1 page.

(Continued)

*Primary Examiner* — Jennifer M Kim

(74) *Attorney, Agent, or Firm* — Kilpatrick Townsend & Stockton LLP

(57) ABSTRACT

The present invention provides a method for altering the pharmacokinetics of mifepristone upon oral administration. Mifepristone absorption into the blood is increased upon administration with meals. The method of the invention can benefit patients suffering from conditions including psychiatric illnesses and hormonal disorders.

11 Claims, No Drawings

(56) References Cited

OTHER PUBLICATIONS

Kawai et al., "Pharmacokinetic Properties of the Antiglucocorticoid and Antiprogesterone Steroid RU 486 in Man", The Journal of Pharmacology and Experimental Therapeutics, vol. 241, No. 2, 1987, pp. 401-406.
Lee et al., Office of Clinical Pharmacology Review, NDA 20687 (Addendum, Korlym™, Mifepristone), 2012, pp. 1-119.
Sarkar, "Mifepristone: Bioavailability, Pharmacokinetics and Use-Effectiveness", European Journal of Obstetrics and Gynecology and Reproductive Biology, vol. 101, Issue No. 2, Mar. 10, 2002, pp. 113-120.
Tsigos, "Differential Diagonsis and Management of Cushing's Syndrome", Annu. Rev. Med., vol. 47, 1996, pp. 443-461.
Winstanley et al., "The Effects of Food on Drug Bioavailability", British Journal of Clinical Pharmacology, vol. 28, 1989, pp. 621-628.
Aanderud, S., et al., *Plasma Cortisol Concentrations after Oral Substitution of Cortisone in the Fasting and Non-Fasting State*, Acta Med Scand 210:157-61 (1981).
Bagchus, W., et al., *Important Effect of Food on the Bioavailability of Oral Testosterone Undecanoate*, Pharmacotherapy 23(3):319-25 (2003).
Belanoff, J., et al., *An Open Label Trial of C-1073 (Mifepristone) for Psychotic Major Depression*, Soc'y Biol. Psychiatry 52:386-92 (2002).
Berthois, Y., et al., *A multiparametric analysis of endometrial estrogen and progesterone receptors after the postovulatory administration of mifepristone*, Fertility & Sterility 55(3):547-54 (1991).
Cassier, P., et al., *Mifepristone for ectopic ACTH secretion in metastic endocrine carcinomas: report of two cases*, Eur. J. Endocrin. 158:935-38 (2008).
Castinetti, F., et al., *Merits and pitfalls of mifepristone in Cushing's syndrome*, Eur. J. Endocrin. 160:1003-10 (2009).
Castinetti, F., et al., *Medical Treatment of Cushing's Syndrome: Glucocorticoid Receptor Antagonists and Mifepristone*, Neuroendocrinology 92:125-30 (2010).
Davis, J., et al., *Guidelines for Counselling Patients Receiving Drugs Used in the Treatment of Neoplastic Disease: a Pharmacist's Guide to Advisory Labels and Patient Information*, Austl. J. Hosp. Pharm., 31:51-55 (2001).
De Lignières, B., et al., *Oral Micronized Progesterone*, Clinical Therapeutics, 21(1):41-60 (1999).
Heikinheimo, O., et al., *Clinical Pharmacokinetics of Mifepristone*, Clin. Pharmacokinet. 33(1):7-17 (1997).
Heikinheimo, O., et al., *The pharmacokinetics of mifepristone in humans reveal insights into differential mechanisms of antiprogestin action*, Contraception, 68:421-26 (2003).
Johanssen, S., et al., *Mifepristone (RU 486)* in Cushing's syndrome, Eur. J. Endocrin. 157:561-69 (2007).
Lindberg, C., *Emergency Contraception: The Nurse's Role in Providing Postcoital Options*, J. Obstestric, Gynecologic & Neonatal Nurs., 26:146-52 (1997).
Luft, F., *Novel cell therapy for type 1 diabetes mellitus*, J. Mol. Med., 87:659-61 (2009).
Nieman, L., et al., *Successful Treatment of Cushing's Syndrome with the Glucocorticoid Antagonist RU 486*, J. Clin. Endocrinol. & Metab., 61:536-40 (1985).
Para, M., et al., *Phase I/II Trial of the Anti-HIV Activity of Mifepristone in HIV Infected Subjects ACTG 5200*, J. Acquir Immune Defic Syndr. 53(4):491-95 (2010).
Sääv, I., et al., *Medical abortion in lactating women—low levels of mifepristone in breast milk*, Acta Obstetricia et Gynecologica, 89:618-22 (2010).
Sartor, O., et al., *Mifepristone: Treatment of Cushing's Syndrome*, Clinical Obstetrics & Gynecology, 39:506-10 (1996).
Sitruk-Ware, R. & Spitz, I.M., *Pharmacological properties of mifepristone: toxicology and safety in animal and human studies*, Contraception 68:409-20, (2003) (TEVA_MIFE-0072018-029).
Welling, PG "Effects of Food on Drug Absorption" Annu Rev Nutr 16:383-415 (1996).

OPTIMIZING MIFEPRISTONE ABSORPTION

CROSS-REFERENCES TO RELATED APPLICATIONS

This application is a continuation of U.S. application Ser. No. 13/677,465, filed Nov. 15, 2012, which claims priority to U.S. Provisional Application No. 61/561,644, filed Nov. 18, 2011, each of which is incorporated in its entirety herein for all purposes.

BACKGROUND OF THE INVENTION

The term "food effect" refers to a somewhat unpredictable phenomenon that can influence the absorption of drugs from the gastrointestinal tract following oral administration. A food effect can be designated negative when absorption is decreased, or positive when absorption is increased and manifested as an increase in oral bioavailability (as reflected by total exposure). Alternatively, food effects can refer to changes in maximum concentration, or the time to reach maximum concentration, independently of overall absorption. As a result, some drugs have to be taken in either fasted or fed conditions to achieve the optimum effect. For example, patients may be instructed to take a drug with a meal, before a meal (e.g., one hour before a meal), or after a meal (e.g., two hours after a meal). However, many drugs are unaffected by food, and thus, can be taken in either a fasted or a fed condition.

Mifepristone is a synthetic steroid that binds progesterone and glucocorticoid receptors and has been employed to treat a number of conditions including meningioma, uterine fibroids, hyperadrenocorticism, and certain psychiatric illnesses. It has been surprisingly discovered that administration of the same dose of mifepristone can produce widely varying plasma drug concentration in different patients. For the same dose of mifepristone, the plasma drug concentration can differ by as much as 800% from one patient to another. The varied plasma drug concentration can result in some patients not receiving an efficacious dose of mifepristone. For these patients in particular, it is necessary to improve the pharmacokinetics of mifepristone upon administration. Surprisingly, the present invention meets this and other needs.

BRIEF SUMMARY OF THE INVENTION

In one embodiment, the present invention provides a method for increasing mifepristone absorption in a patient suffering from a disorder or condition amenable to treatment by mifepristone. The method includes administering a dosage of from about 100 to about 2000 mg mifepristone to the patient within 1 hour of consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption in the patient.

In a second embodiment, the invention provides a method for improving absorption of mifepristone in a patient suffering from psychotic major depression. The method includes administering a dose of from about 100 mg to about 2000 mg mifepristone to the patient within 1 hour after consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption.

In a third embodiment, the invention provides a method of improving absorption of mifepristone in a patient suffering from Cushing's Syndrome. The method includes administering a dose of from about 100 mg to about 2000 mg mifepristone to the patient within 1 hour after consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption.

DETAILED DESCRIPTION OF THE INVENTION

I. General

The present invention provides a method for altering the pharmacokinetics of mifepristone upon oral administration. Mifepristone absorption into the blood of a patient is increased upon administration following a meal, serving to enhance the therapeutic benefit of a given dose as well as prevent adverse effects associated with higher dosages. The methods of the invention can be of special benefit to patients suffering from psychiatric illnesses and endocrine disorders.

II. Definitions

The term "mifepristone" refers to a compound having the following structure:

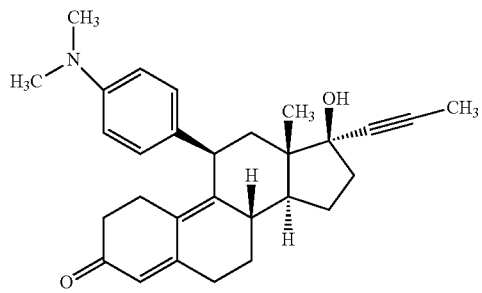

The term mifepristone also refers to a family of compositions also known as: RU486 or RU38.486; 17-beta-hydroxy-11-beta-(4-dimethyl-aminophenyl)-17-alpha-(1-propynyl)-estra-4,9-dien-3-one); 11-beta-(4dimethylaminophenyl)-17-beta-hydroxy-17-alpha-(1-propynyl)-estra-4,9-dien-3-one); 11B-[p-(Dimethylamino) phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy-11B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11B,17B)-11-[4-dimethylamino)-phenyl]-17-hydroxy-17-(1-propynyl)estra-4,9-dien-3-one; and 11B-[4-(N,N-dimethylamino) phenyl]-17A-(prop-1-ynyl)-D-4,9-estradiene-17B-ol-3-one. Salts, hydrates and prodrug forms of mifepristone are also useful in the formulations of the present invention.

Mifepristone and its analogs bind to the glucocorticoid receptor (GR), typically with high affinity, and inhibit the biological effects initiated/mediated by the binding of any cortisol or cortisol analogue to the GR. As such, mifepristone has been used to treat conditions associated with elevated cortisol levels including, for example, hyperadrenocorticism, also known as Cushing's syndrome (Chrousos, pp 273-284, In: Baulieu, ed. *The Antiprogestin Steroid RU 486 and Human Fertility Control*. Plenum Press, New York (1989), Sartor (1996) *Clin. Obstetrics and Gynecol.* 39:506-510). Patients with some forms of psychiatric illnesses can be responsive to treatments which block the effect of cortisol, as by administering GR antagonists (Van Look (1995) Human Reproduction Update 1:19-34). In one study, a patient with depression associated with Cushing's Syndrome was responsive to a high dose, up to 1400 mg per day, of mifepristone (Nieman (1985) *J. Clin Endocrinol. Metab.* 61:536). Due to its antiprogestogenic activity, mifepristone has also been employed in emergency contraception, medical abortion, and treatment of uterine fibroids and meningioma (Healy (2009) *Australian Prescriber* 32:152-154).

The term "increasing mifepristone absorption" refers to promoting the entrance of mifepristone into blood upon administration to the subject. "Improving mifepristone absorption" refers to increasing the level of mifepristone in the bloodstream of a subject treated via the method of the invention.

The term "meal" refers to a meal as defined by the FDA food effect test guidelines and can include a high-fat, low-fat or other type of meal. A high-fat meal is one where approximately 50 percent of total caloric content of the meal is fat. Also included are high-calorie meals having approximately 800 to 1000 calories. The meal can have approximately 150, 250, and 500-600 calories from protein, carbohydrate, and fat, respectively. An example test meal includes two eggs fried in butter, two strips of bacon, two slices of toast with butter, four ounces of hash brown potatoes and eight ounces of whole milk. Another example of a meal includes a moderate fat breakfast (34% of total calories from fat), which on average contains 27 g protein (13%), 32 g fat (34%), and 111 g carbohydrate (53%), totaling approximately 836 calories.

The term "$C_{max}$" refers to the maximum observed plasma concentration of mifepristone resulting from administration via a method of the present invention or via an alternative route.

The term "area under the curve" (AUC) refers to the integral of a plot of mifepristone concentration in plasma vs. time during or after administration.

The term "patient" refers to animals such as mammals, including, but not limited to, primates (e.g., humans), cows, sheep, goats, horses, dogs, cats, rabbits, rats, mice and the like. The patient can have a condition known to be treated by glucocorticoid antagonists such as mifepristone. Such conditions include, but are not limited to, psychiatric illnesses and hormonal disorders. In certain embodiments, the patient is a human. The patient can be male or female.

The term "administering mifepristone without food" refers to administering mifepristone more than one hour after food has been ingested by the patient to whom it is administered. "Administration of mifepristone in the absence of the meal" refers to mifepristone administration without prior consumption of a meal by a patient under the same conditions as those after which increased mifepristone absorption is observed. The conditions include, but are not limited to, the nutritional content of the meal and the timing with respect to mifepristone administration.

The term "oral dosage form" refers to a formulation or preparation of a therapeutic agent suitable for ingestion by a subject via mouth. Preferably, the therapeutic agent is mifepristone. Oral dosage forms can include but are not limited to liquid solutions, suspensions, emulsions, tablets, capsules, and lozenges.

The term "unit dosage form" refers to physically discrete units, such as capsules or tablets suitable as unitary dosages for human patients and other subjects, each unit containing a predetermined quantity of a therapeutic agent calculated to produce the desired therapeutic effect. Preferably, the therapeutic agent is mifepristone. Unit dosage form can include additional therapeutic agents as well as pharmaceutically acceptable carriers, diluents, excipients, or combinations thereof.

III. Method for Increasing Mifepristone Absorption

The present invention provides a method for increasing mifepristone absorption in a patient suffering from a disorder or condition amenable to treatment by a glucocorticoid receptor antagonist (GRA) using any suitable dosage of mifepristone by administering the mifepristone following consumption of food by the patient. In some embodiments, the present invention provides a method for increasing mifepristone absorption in a patient suffering from a disorder or condition amenable to treatment by mifepristone, including administering to the patient a dosage of from about 100 to about 2000 mg mifepristone within 1 hour of consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption in the patient.

A. Formulations and Administration

Mifepristone can be administered at any suitable dosage in the method of the present invention. In some embodiments, mifepristone can be administered at a dosage of about 100 mg to about 2000 mg. In other embodiments, dosages of 100, 200, 300, 400, 500, 600, 700, 800, 900, 1000, 1100, 1200, 1300, 1400, 1500, 1600, 1700, 1800, 1900, or 2000 mg can be used. In some embodiments, the dosage is of from about 300 to about 1600 mg mifepristone. In some embodiments, the dosage is of from about 300 to about 900 mg mifepristone. In some embodiments, the dosage is of from about 500 to about 700 mg mifepristone. In some embodiments, the dosage is of from about 900 to about 1500 mg mifepristone. In some embodiments, the dosage is of from about 1100 to about 1300 mg mifepristone. In some embodiments, the dosage is of from about 500 to about 1500 mg mifepristone. In some embodiments, the dosage is of from about 400 to about 800 mg mifepristone. In some embodiments, the dosage is of about 600 mg mifepristone. In some embodiments, the dosage is of from about 1000 to about 1400 mg mifepristone. In some embodiments, the dosage is of about 1200 mg mifepristone. The dosages, however, can be varied depending upon the requirements of the patient and the condition being treated. The dose administered to a patient, in the context of the present invention, should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner.

The mifepristone can be administered by any suitable means. Formulations of the present invention include mifepristone in combination with pharmaceutical excipients.

Mifepristone is commercially available from a variety of sources such as Eurolabs Ltd. (London, England). Mifepristone can also be synthesized by one of skill in the art using known synthetic procedures. Details on techniques for formulation and administration are well described in the scientific and patent literature, see, e.g., the latest edition of Remington's Pharmaceutical Sciences, Maack Publishing Co, Easton Pa. ("Remington's").

Oral dosage forms can consist of formulations including (a) liquid solutions, such as an effective amount of mifepristone suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Single or multiple doses of mifepristone formulations can be administered depending on the dosage and frequency as required and tolerated by the patient. Mifepristone can be administered for any period of time, such as at least 1 day. In further embodiments, mifepristone can be administered for 2, 3, 4, 5, or 6 days. In certain embodiments of the invention, mifepristone is administered daily for at least 7 days. Mifepristone can also be administered using more daily doses over a longer period of time, such as via 28 daily doses over a period of 28 days. Longer times for administration of mifepristone are also within the scope of the present invention.

Oral bioavailability refers to the fraction of mifepristone absorbed by a subject upon mifepristone administration via a method of the present invention. Bioavailability is reflected in the observed "exposure" which is measured as the integral of a plot of mifepristone concentration in plasma vs. time during or after administration. This integral is referred to as the "area under the curve" or AUC. As used herein, "exposure" in synonymous with "AUC." In some embodiments of the invention, absolute bioavailability can be assessed by comparing the AUC resulting from the method of the invention with the AUC resulting from intravenous mifepristone administration. In certain embodiments of the invention, relative bioavailability can be assessed by comparing the AUC resulting from the method of the invention with the AUC resulting from mifepristone administration via an alternative route. The term "$C_{max}$" refers to the maximum observed plasma concentration of mifepristone resulting from administration via a method of the present invention or via an alternative route.

The method of the present invention includes administration of mifepristone within 1 hour of a consuming a meal and is sufficient to increase $C_{max}$ and AUC values as compared to those values resulting from administration of mifepristone without food. $C_{max}$ and AUC can increase by any amount including 1%, 2%, 3%, 4%, 5%, 10%, 15%, 20%, 25%, 30%, 35%, 40%, 45%, and 50%. Increases greater than 50% can also occur according to the method of the invention. In some embodiments, the $C_{max}$ increases by at least 5% compared to the administration of mifepristone in the absence of the meal. In some embodiments, the $C_{max}$ increases by at least 15% compared to the administration of mifepristone in the absence of the meal. In some embodiments, the $C_{max}$ increases by at least 15% compared to the administration of mifepristone in the absence of the meal. In some embodiments, the AUC increases by at least 5% compared to the administration of mifepristone in the absence of the meal. In some embodiments, the AUC increases by at least 15% compared to the administration of mifepristone in the absence of the meal. In some embodiments, the AUC increases by at least 25% compared to the administration of mifepristone in the absence of the meal. In some embodiments, the $C_{max}$ increases by at least 5% and the AUC increases by at least 5% compared to the administration of mifepristone in the absence of the meal. In some embodiments, the $C_{max}$ increases by at least 15% and the AUC increases by at least 15% compared to the administration of mifepristone in the absence of the meal. In some embodiments, the $C_{max}$ increases by at least 25% and the AUC increases by at least 25% compared to the administration of mifepristone in the absence of the meal.

The meal can be any suitable meal. Suitable meals can be high fat meals, moderate fat meals, low fat meals, or meals without any fat. Other suitable meals include high calorie meals. A high-fat meal is one where approximately 50 percent of total caloric content of the meal is fat. A high-calorie meal includes approximately 800 to 1000 calories. The meal can have approximately 150, 250, and 500-600 calories from protein, carbohydrate, and fat, respectively. An example test meal includes two eggs fried in butter, two strips of bacon, two slices of toast with butter, four ounces of hash brown potatoes and eight ounces of whole milk. Another example of a meal includes a moderate fat breakfast (34% of total calories from fat). Other meals useful in the present invention are known to one of skill in the art.

B. Patients in Need

A patient according to the present invention is a subject in need of mifepristone administration. Preferably, the patient is a mammal having a condition known to be treated by glucocorticoid antagonists such as mifepristone. Such conditions include, but are not limited to, psychiatric illnesses and endocrine disorders. Most preferably, the patient is a human. In one embodiment of the present invention, the patient is a male.

Patients amenable to treatment with mifepristone according to the methods of the present invention suffer from conditions including, but not limited to, obesity, diabetes, cardiovascular disease, hypertension, Syndrome X, depression, psychotic major depression, anxiety, psychotic major depression, Cushing's syndrome, glaucoma, human immunodeficiency virus (HIV) or acquired immunodeficiency syndrome (AIDS), neurodegeneration, Cushings disease, Alzheimer's disease, Parkinson's disease, cognition enhancement, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches.

In some embodiments, the patient suffers from a mental or neurological disorder or condition such as depression, psychotic major depression, anxiety, neurodegeneration, Parkinson's disease, Alzheimer's disease, compulsive behavior, addiction, psychosis, anorexia, cachexia, post-traumatic stress syndrome, cognition enhancement, mild cognitive impairment, psychosis, dementia, delirium, cognitive impairment in depressed patients, cognitive deterioration in individuals with Down's syndrome, psychosis associated with interferon-alpha therapy, postpartum psychosis, postpartum depression, or neurological disorders in premature infants.

In other embodiments, the patient suffers from a metabolic or cardiovascular disorder or condition such as obesity, diabetes, hyperglycemia, antipsychotic induced weight gain, cardiovascular disease, or hypertension.

In some embodiments, the patient suffers from a viral or immune disorder or condition such as viral infection, human immunodeficiency virus (HIV) or acquired immunodeficiency syndrome (AIDS), immunodeficiency, immunomodulation, or autoimmune diseases.

In some embodiments, the patient suffers from a bone or inflammatory disorder or condition such as post-surgical bone fracture, osteoporosis, frailty, muscle frailty, inflammatory diseases, asthma and rhinitis, osteoarthritis, or rheumatoid arthritis.

In some embodiments, the patient suffers from a disease or condition such as Syndrome X, Addison's Disease, adrenal function-related ailments, glaucoma, allergies, wound healing, multi-drug resistance, medical catabolism, stress disorders, chronic pain, pain associated with gastroesophageal reflux disease, or migraine headaches.

The term "psychotic major depression," also referred to as "psychotic depression" (Schatzberg (1992) Am. J. Psychiatry 149:733-745), "psychotic (delusional) depression" (Ibid.), "delusional depression" (Glassman (1981) supra) and, "major depression with psychotic features" (see the DSM-III-R), refers to a distinct psychiatric disorder which includes both depressive and psychotic features. Individuals manifesting both depression and psychosis, i.e. psychotic depression, are herein referred to as "psychotic depressives." It has been long-recognized in the art as a distinct syndrome, as described, for example, by Schatzberg (1992) supra. Illustrative of this distinctness are studies which have found significant differences between patients with psychotic and nonpsychotic depression in glucocorticoid activity, dopamine-beta-hydroxylase activity, levels of dopamine and serotonin metabolites, sleep measures and ventricle to brain ratios. Psychotic depressives respond very differently to treatment compared to individuals with other forms of depression, such as "non-psychotic major depression." Psychotic depressives have a low placebo response rate and respond poorly to antidepressant therapy alone (without concurrent antipsychotic treatment). Psychotic depressives are markedly unresponsive to tricyclic (anti-depressive) drug therapy (Glassman, et al. (1975) supra). While psychotic depressives can respond to electroconvulsive therapy (ECT), their response time is relatively slow and the ECT has a high level of related morbidity. Clinical manifestations and diagnostic parameters of "psychotic major depression" is described in detail in the DSM-IV (Kaplan, ed. (1995) supra). Thus, due to its unique pathophysiology, high rate of morbidity and response to treatment, there is great practical need to differentially diagnose and specifically treat psychotic major depression as compared to non-psychotic depression.

In some embodiments, the present invention provides a method for improving absorption of mifepristone in a patient suffering from psychotic major depression. The method includes the administration of a dose of from about 100 mg to about 2000 mg mifepristone to the patient within 1 hour after consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption.

Cushing's syndrome is a endocrine disease with an estimated incidence of approximately 10 per 1 million persons (Meier and Biller (1997) Endocrinol Metab Clin North Am 26:741-762). Cushing's syndrome is associated with an increased blood concentration of cortisol (hypercortisolism) or the presence in blood of glucocorticoid hormone excess over a long period of time. Cushing's syndrome is classified as either ACTH dependent or non ACTH dependent. ACTH dependent Cushing's syndrome is characterized by a chronic ACTH hypersecretion which stimulates the growth of the adrenal glands and the hypersecretion of corticosteroids. The most common underlying cause of ACTH dependent Cushing's syndrome is excessive production of ACTH by pituitary adenomas known as Cushing's disease. Cushing's syndrome resulting from the production of ACTH in another location than the pituitary gland is known as ectopic Cushing's syndrome. Examples of ectopic sites include thymoma, medullary carcinoma of the thyroid, pheochromocytoma, islet cell tumors of the pancreas and small cell carcinoma of the lung. ACTH independent Cushing's syndromes are caused by adrenal tumors that can be either adenomas or carcinomas. Both adrenal adenomas and carcinomas are characterized by chronic cortisol hypersecretion.

Symptoms of Cushing's syndrome include a characteristic abnormal fat deposition around the neck, thinning of the skin, osteoporosis, moon face, weakness, fatigue, backache, headache, impotence, muscle atrophy, increased thirst, urination, insulin resistance, dyslipidemia, myopathy, amenorrhea, hypertension, weight gain, central obesity, steroid hypersecretion, elevated urinary cortisol excretion and mental status changes, in particular depression (Orth (1995) N. Engl. J. Med. 332:791-803; Dahia and Grossman (1999) Endocr. Rev. 20:136-55).

In some embodiments, the present invention provides a method for improving absorption of mifepristone in a patient suffering from Cushing's syndrome. The method includes the administration of a dose of from about 100 mg to about 2000 mg mifepristone to the patient within 1 hour after consuming a meal, such that the pharmacokinetics of mifepristone are altered by increasing the maximum plasma concentration ($C_{max}$) and increasing the area under the curve (AUC) compared to administering mifepristone without food, thereby increasing mifepristone absorption.

C. Assay for Testing Mifepristone Levels

Mifepristone levels can be determined by any method known in the art. Methods for detecting mifepristone levels include, but are not limited to, radio-immuno assay and mass spectrometry (MALDI, SELDI, LS/MS, LS/MS/MS, among others). Liquid chromatography mass spectrometry (LC/MS or LC-MS) separates compounds chromatographically before they are introduced to the ion source and mass spectrometer. It differs from GC/MS in that the mobile phase is liquid, usually a combination of water and organic solvents, instead of gas. Most commonly, an electrospray ionization source is used in LC/MS.

Tandem mass spectrometry (MS/MS) involves multiple steps of mass selection or analysis, usually separated by some form of fragmentation. A tandem mass spectrometer is one capable of multiple rounds of mass spectrometry. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then catalogs the fragments produced from the peptides. Tandem MS can also be done in a single mass analyzer over time as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD) and blackbody infrared radiative dissociation (BIRD). One of skill in the art will appreciate that other assays for testing mifepristone levels are known to one of skill in the art.

In some embodiments, the assay can be performed as follows. Blood is collected from a patient in a vacutainer containing sodium heparin. The blood is centrifuged and the resulting plasma frozen at an appropriate temperature until assay. In some embodiments, the temperature is about −70° C. In other embodiments, other blood components can be collected and stored. Prior to analysis, the plasma is thawed and a fraction of the plasma is mixed with an internal standard in a solvent such as acetonitrile, to obtain a fixed concentration of the standard. In some embodiments, the internal standard can be mifepristone-$d_4$. The concentration of the internal standard is selected in order to be greater than the expected concentration of mifepristone in the plasma. For example, the internal standard can have a concentration of 2000 ng/mL. One of skill in the art will appreciate that other internal standards, and other concentrations, are useful in the present invention.

Base is then added to the sample solution. The base can be any amine or ammonium base, such as ammonium hydroxide. One of skill in the art will appreciate that other bases are useful in the present invention.

Solvent is then added to the solution and the mifepristone (along with the internal standard) are extracted from the plasma. Solvents useful for the extraction of mifepristone include, but are not limited to, hexanes, pentanes, ethers (such as diethylether, tetrahydrofuran and methyl-t-butyl ether (MTBE)), ethyl acetate, chloroform and methylene chloride. One of skill in the art will appreciate that other solvents are useful in the present invention.

Following separation and concentration of the organic layer, the sample is reconstituted in a solvent mixture comprising water, acetonitrile and formic acid. The ratio of the solvent components can vary. In some embodiments, the solvent mixture is water:acetonitrile:formic acid (75:25:0.1, v/v/v). One of skill in the art will appreciate that other solvent mixtures are useful in the present invention.

The sample can then be analyzed by reverse-phase high pressure liquid chromatography (HPLC). In some embodiments, the reverse-phase HPLC is performed using a water:acetonitrile:formic acid (60:40:0.1) mobile phase (isocratic) at a flow rate of 0.3 mL/min. One of skill in the art will appreciate that other mobile phases and flow rates are useful in the present invention.

The reverse-phase HPLC column can be a phenyl column maintained at 50° C. Mifepristone elutes at 4.2 minutes. Following elution, the mobile phase can be nebulized using heated nitrogen in a Z-spray source/interface and the ionized compounds detected using a tandem quadrupole mass spectrometer. Mifepristone (molecular weight of 430 g/mol) can be detected at m/z 372.30. The internal standard mifepristone-$d_4$ can be detected at m/z 376.30. The ratio of the mifepristone peak height to the peak height for the internal standard can then be calculated.

The plasma concentration of mifepristone is then calculated by comparing the experimental ratio to a standard curve of mifepristone:mifepristone-$d_4$ peak height ratio v. mifepristone concentration. The standard curve is generated by first measuring the mifepristone:mifepristone-$d_4$ peak height ratios for mifepristone samples at 10, 20, 50, 100, 200, 500, 1000 and 2000 ng/mL where the mifepristone-$d_4$ internal standard has a concentration of 2000 ng/mL. The mifepristone:mifepristone-$d_4$ peak height ratios of these known solutions are then fit to a power equation (Mass Lynx by Micromass, Beverly, Mass.), against which future samples with unknown concentrations of mifepristone are compared.

IV. Examples

Example 1. Food Effect Studies

Multiple studies evaluated the effect of food on the pharmacokinetics of mifepristone and its metabolites. In all studies, healthy adults were randomized to a sequence of administration of mifepristone drug product under fasting and fed conditions.

Fed Group (50% Fat)

Studies C1073-12 and C1073-20 evaluated the effects of a standardized high-fat (50% fat), high calorie breakfast on the pharmacokinetics of single 600 mg doses of mifepristone tablets and 1200 mg doses of mifepristone, respectively. Study C1073-27 evaluated the pharmacokinetic effects of a typical breakfast (34% fat) administered during 7 days of multiple dose administration (mifepristone 1200 mg/day) followed by a standardized high-fat (50% fat) breakfast on the eighth day. In all three studies, the fed state increased plasma mifepristone $C_{max}$ and exposure in comparison to the fasted state, and the point estimate for the size of the effect was consistently larger for AUC than that for $C_{max}$. In the single dose studies, the increases in $C_{max}$ and exposure with food were both numerically larger for the 1200 mg dose of mifepristone compared to that for the 600 mg dose, suggesting a possible dose-related effect. Multiple dosing of mifepristone at 1200 mg/day for 7 days with typical fat meals showed a mean 65% increase in mifepristone exposure relative to 7 days of administration in the fasted state. Switching to administration with a high fat meal on day 8 after 7 days of administration with typical fat meals had little or no effect on either $C_{max}$ or exposure, indicating that fat content is not a major factor in producing the fed/fasted difference.

Fed Group (34% Fat)

Data have also been obtained on the effect of a moderate fat (34% fat) breakfast on the PK of mifepristone following mifepristone doses of 600 mg/day for 7 days. These data were obtained from cohort 3 of a Phase I clinical pharmacology trial (Study CORT-108297-102).

The test group was comprised of 10 healthy adult subjects who were randomized to receive mifepristone at 600 mg/day for up to 14 days in Cohort 3 of Study CORT-108297-102. For this comparison the PK data after 7 days of dosing were used. Subjects were given a moderate fat breakfast (34% of total calories from fat), which on average contained 27 g protein (13%), 32 g fat (34%), and 111 g carbohydrate (53%), totaling approximately 836 calories. The meal was given every day at approximately 30 min prior to receiving mifepristone, which was dosed as two 300 mg tablets once daily.

Day 7 PK parameters from two historical studies (Studies C-1073-05 and C-1073-300 Part II) were used as the reference group for this analysis. In these studies, a total of 52 healthy adults received 600 mg/day of mifepristone for at least 7 days in the fasted.

Demographics across the test and reference groups were similar for weight, height, and body mass index (BMI), based on mean and median values and the overlap of 95% confidence intervals about the mean. In the fed group, there were 5 Caucasians (50%), 2 Hispanics (20%), and 3 African Americans (30%). In the combined reference group, there were 31 Caucasians (59.6%), 8 Hispanics (15.4%), 4 African Americans (7.7%), 3 Asians (5.8%) and 6 subjects of other ethnicities (11.5%). Thus, Caucasians accounted for approximately half of the subjects in both the fed and fasted groups, with the remaining subjects representing a racially/ethnically diverse population. Gender was mostly male in both groups.

In this food effect study of doses of 600 mg/day for 7 days, Day 7 PK parameters of mifepristone under fed conditions (34% fat breakfast) (CORT-108297-102) were compared to fasting conditions using historical data from Studies C-1073-05 and C-1073-300, Part II. Dosing with mifepristone 600 mg/day for 7 days following a breakfast of 34% fat (a moderate fat meal) yielded increases in mifepristone $C_{max}$ and $AUC_{0-24}$ of 34% and 44%, respectively, as compared to the same dose in the fasted state. Thus, mifepristone plasma $C_{max}$ and AUC are higher when the drug is taken in the fed state as compared to the fasted state.

Mifepristone pharmacokinetics after multiple dosing of mifepristone show strong lack of dose proportionality, with little increase in exposure or $C_{max}$ as dose increases above 600 mg. The effect of food on exposure and $C_{max}$ at doses above 600 mg is considerably larger than that which can be achieved by dose increase alone for mifepristone administered in the fasted state. Results of the 90% confidence interval testing for the 3 food effect studies are provided for mifepristone in Table 1.

TABLE 1

90% Confidence Intervals for Mifepristone PK Parameters in Food Effect Studies and Studies with Food Effect Assessments

| Parameter | Dose | Condition | % Fat | N | Geo Mean | Ratio of Geometric Means | 90% CI | Study |
|---|---|---|---|---|---|---|---|---|
| Cmax (ng/mL) | 600 mg single dose | Fast | | 49 | 2306 | 1.19 | 1.06-1.33 | 12 |
| | | Fed | 50% | 49 | 2735 | | | |
| | 1200 mg single dose | Fast | | 23 | 2828 | 1.30 | 1.24-1.65 | 20 |
| | | Fed | 50% | 22 | 3663 | | | |
| | 1200 mg/day × 7 days | Fast | | 22 | 3223 | 1.56 | 1.41-1.74 | 27 |
| | | Fed | 34% | 24 | 5039 | | | |
| | 600 mg/day × 7 days | Fast | | 52 | 3041 | 1.34 | 1.10-1.63 | C3* |
| | | Fed | 34% | 10 | 4072 | | | |
| AUCinf (hr * ng/mL) | 600 mg single dose | Fast | | 49 | 103905 | 1.29 | 1.15-1.45 | 12 |
| | | Fed | 50% | 49 | 134083 | | | |
| | 1200 mg single dose | Fast | | 22 | 133881 | 1.42 | 1.23-1.65 | 20 |
| | | Fed | 50% | 22 | 190638 | | | |
| AUC0-24 (hr * ng/mL) | 1200 mg/day × 7 days | Fast | | 22 | 44174 | 1.65 | 1.52-1.79 | 27 |
| | | Fed | 34% | 24 | 72766 | | | |
| | 600 mg/day × 7 days | Fast | | 52 | 43564 | 1.44 | 1.17-1.76 | C3* |
| | | Fed | 34% | 10 | 62579 | | | |

*C3 = Cohort 3 from Phase I study CORT-108297-102. Comparison was to combined data in healthy Example 2. Treatment of Male Patient with Psychotic Major Depression A 50 year-old male, weighing 175 pounds, presents to a physician with psychotic major depression (PMD). The physician prescribes 600 mg of mifepristone to be taken daily over a period of seven days within 1 hour of eating a normal breakfast.

Example 3. Treatment of Male Patient with Cushing's Syndrome

A 50 year-old male, weighing 175 pounds, presents to a physician with Cushing's syndrome. The physician prescribes 600 mg of mifepristone to be taken daily over a period of seven days within 1 hour of eating a normal breakfast.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of improving absorption of mifepristone in a patient suffering from Cushing's Syndrome, comprising administering to the patient for at least 7 days an oral dose of mifepristone of 900 mg per day within about 30 minutes after consuming a meal, such that the pharmacokinetics of mifepristone absorption are altered by increasing the maximum plasma concentration ($C_{max}$) and increasing the area under the curve (AUC) as compared to the $C_{max}$ and AUC that would result from administering mifepristone without food in the fasted state in the absence of the meal, said increase in AUC being at least 44%, and thereby improving mifepristone absorption in the patient.

2. The method of claim 1, wherein the patient suffers from Cushing's disease.

3. The method of claim 1, wherein the daily oral dose of mifepristone is administered for at least 28 days.

4. The method of claim 1, wherein the mifepristone is administered as a single dose.

5. The method of claim 1, wherein the increase in AUC is between 44% and about 65%.

6. The method of claim 1, wherein the increase in $C_{max}$ is at least 34%.

7. The method of claim 1, wherein the increase in $C_{max}$ is between 34% and about 56%.

8. The method of claim 5, wherein the increase in $C_{max}$ is at least 34%.

9. The method of claim 5, wherein the increase in $C_{max}$ is between 34% and about 56%.

10. The method of claim 1, wherein the patient is a male.

11. The method of claim 1, wherein the patient is a female.

* * * * *